(12) United States Patent
Chartres et al.

(10) Patent No.: US 10,058,389 B2
(45) Date of Patent: Aug. 28, 2018

(54) ENDOSCOPE VALVE CONTAINER

(71) Applicant: KEYMED (MEDICAL & INDUSTRIAL EQUIPMENT) LTD., Essex (GB)

(72) Inventors: Jonathan Victor Chartres, Devon (GB); Adam Thomas Floyd, Devon (GB)

(73) Assignee: KEYMED (MEDICAL & INDUSTRIAL EQUIPMENT) LTD (GB)

( * ) Notice: Subject to any disclaimer, the term of this patent is extended or adjusted under 35 U.S.C. 154(b) by 339 days.

(21) Appl. No.: 14/552,939

(22) Filed: Nov. 25, 2014

(65) Prior Publication Data
US 2015/0144515 A1    May 28, 2015

(51) Int. Cl.
| | |
|---|---|
| *A61B 50/00* | (2016.01) |
| *A61B 19/02* | (2006.01) |
| *A61L 2/26* | (2006.01) |
| *A61B 1/015* | (2006.01) |
| *A61B 1/12* | (2006.01) |
| *B65D 25/10* | (2006.01) |
| *B65D 51/24* | (2006.01) |

(Continued)

(52) U.S. Cl.
CPC .......... *A61B 19/0256* (2013.01); *A61B 1/015* (2013.01); *A61B 1/121* (2013.01);
(Continued)

(58) Field of Classification Search
CPC ..... A61B 19/0256; A61B 1/121; A61B 1/015; A61B 2019/0201; A61B 19/02; A61B 2019/0232; A61B 50/00; A61B 50/20; A61B 50/30; A61B 50/36; A61B 2050/3008; A61B 2050/3011; B65D 25/108; B65D 51/24
(Continued)

(56) References Cited

U.S. PATENT DOCUMENTS 2,356,078 A * 8/1944 Myers ................. B65D 27/00
                                                    118/425
4,064,254 A   12/1977 Dykstra et al.
(Continued)

FOREIGN PATENT DOCUMENTS

| DE | 102005046251 A1 | 3/2007 |
|---|---|---|
| GB | 2475948 A | 6/2011 |

(Continued)

OTHER PUBLICATIONS

Extended European Search Report; dated Jan. 16, 2015 for Application No. 14194972.7.
(Continued)

*Primary Examiner* — Steven A. Reynolds
(74) *Attorney, Agent, or Firm* — Luedeka Neely Group, PC

(57) ABSTRACT

A single use container (10, 40, 70) for holding a plurality of endoscope valves during a cleaning and disinfection procedure defines a plurality of chambers (34, 64, 84) which are isolated from each other and configured to receive a single valve such that a valve in one chamber cannot contact a valve in another chamber. A plurality of apertures (36, 58, 86) in each chamber allow fluid flow therethrough. A closure device (14, 44, 92) is operable to close each chamber (34, 64, 84). An attachment device (38, 68, 77) is configured for attaching the container (10, 40, 70) to an endoscope and to prevent detachment without breaking of the attachment device (38, 68, 77).

6 Claims, 7 Drawing Sheets

Figure 1B:
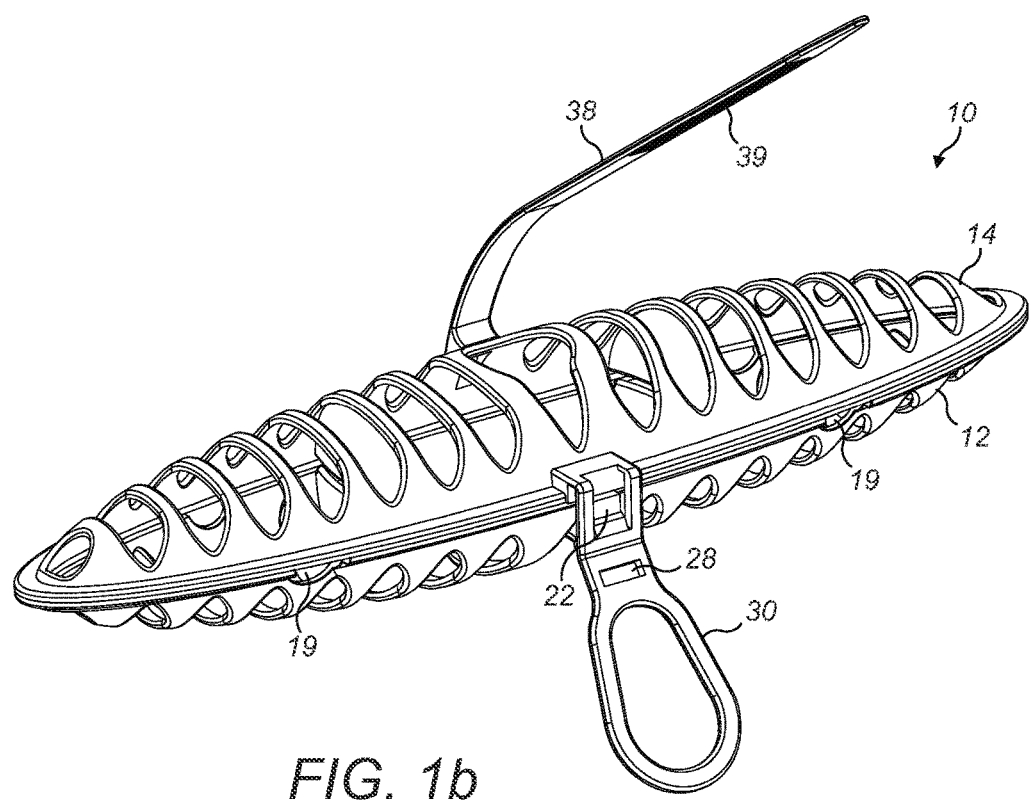

(51) Int. Cl.
*B65D 55/02* (2006.01)
*A61B 50/34* (2016.01)
*A61B 50/20* (2016.01)
*A61B 50/30* (2016.01)
*A61B 90/70* (2016.01)
*A61B 50/33* (2016.01)

(52) U.S. Cl.
CPC .............. *A61B 50/20* (2016.02); *A61B 50/30* (2016.02); *A61B 50/34* (2016.02); *A61L 2/26* (2013.01); *B65D 25/108* (2013.01); *B65D 51/24* (2013.01); *B65D 55/022* (2013.01); *A61B 50/33* (2016.02); *A61B 90/70* (2016.02); *A61B 2050/002* (2016.02); *A61B 2050/005* (2016.02); *A61B 2050/0056* (2016.02); *A61B 2050/0083* (2016.02); *A61B 2050/0084* (2016.02); *A61B 2050/0089* (2016.02); *A61B 2050/314* (2016.02); *A61B 2050/318* (2016.02); *A61L 2202/181* (2013.01); *A61L 2202/24* (2013.01)

(58) Field of Classification Search
USPC .......... 206/370, 570, 362, 363; 383/38, 207, 383/209, 208
See application file for complete search history.

(56) References Cited

U.S. PATENT DOCUMENTS

| | | | |
|---|---|---|---|
| 4,331,257 A | 5/1982 | Taschner | |
| 4,468,811 A | 8/1984 | Shaw et al. | |
| 5,725,097 A | 3/1998 | Bettenhausen et al. | |
| 6,308,875 B1* | 10/2001 | Almo | A41D 13/0012 2/251 |
| 6,391,260 B1* | 5/2002 | Davis | A61L 2/14 206/370 |
| 2003/0217943 A1* | 11/2003 | Sklar | A61B 10/0096 206/438 |
| 2004/0178099 A1* | 9/2004 | Natay-Curley | A61L 2/07 206/370 |
| 2005/0141787 A1* | 6/2005 | Breil, Jr. | B65D 33/2533 383/61.2 |
| 2013/0043155 A1* | 2/2013 | Hartley | A61B 19/0287 206/363 |
| 2015/0101616 A1* | 4/2015 | Wiley | A61B 19/10 128/852 |

FOREIGN PATENT DOCUMENTS

| | | |
|---|---|---|
| GB | 2485011 | 5/2012 |
| GB | 2485818 A | 5/2012 |
| GB | 2513643 A | 5/2013 |
| WO | 9850083 | 11/1998 |
| WO | 2005053597 A2 | 6/2005 |
| WO | 2011107330 A1 | 9/2011 |
| WO | 2011131953 A1 | 10/2011 |
| WO | 2012069800 A1 | 5/2012 |

OTHER PUBLICATIONS

Intellectual Property Office www.ipo.gov.uk Patents Act 1977: Search Report under Section 17 Application No. GB1321017.4 date of search Jun. 18, 2014.

* cited by examiner

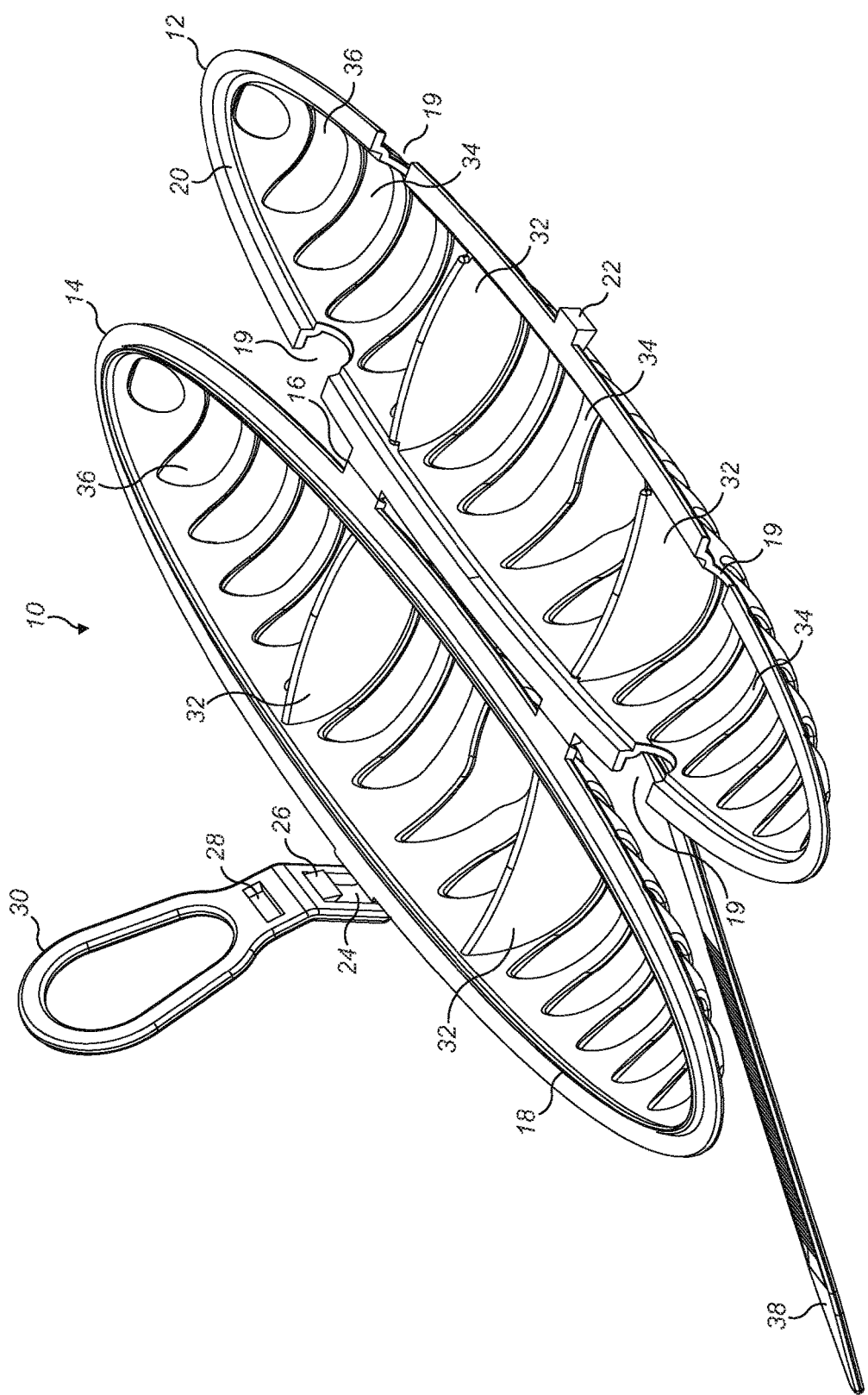

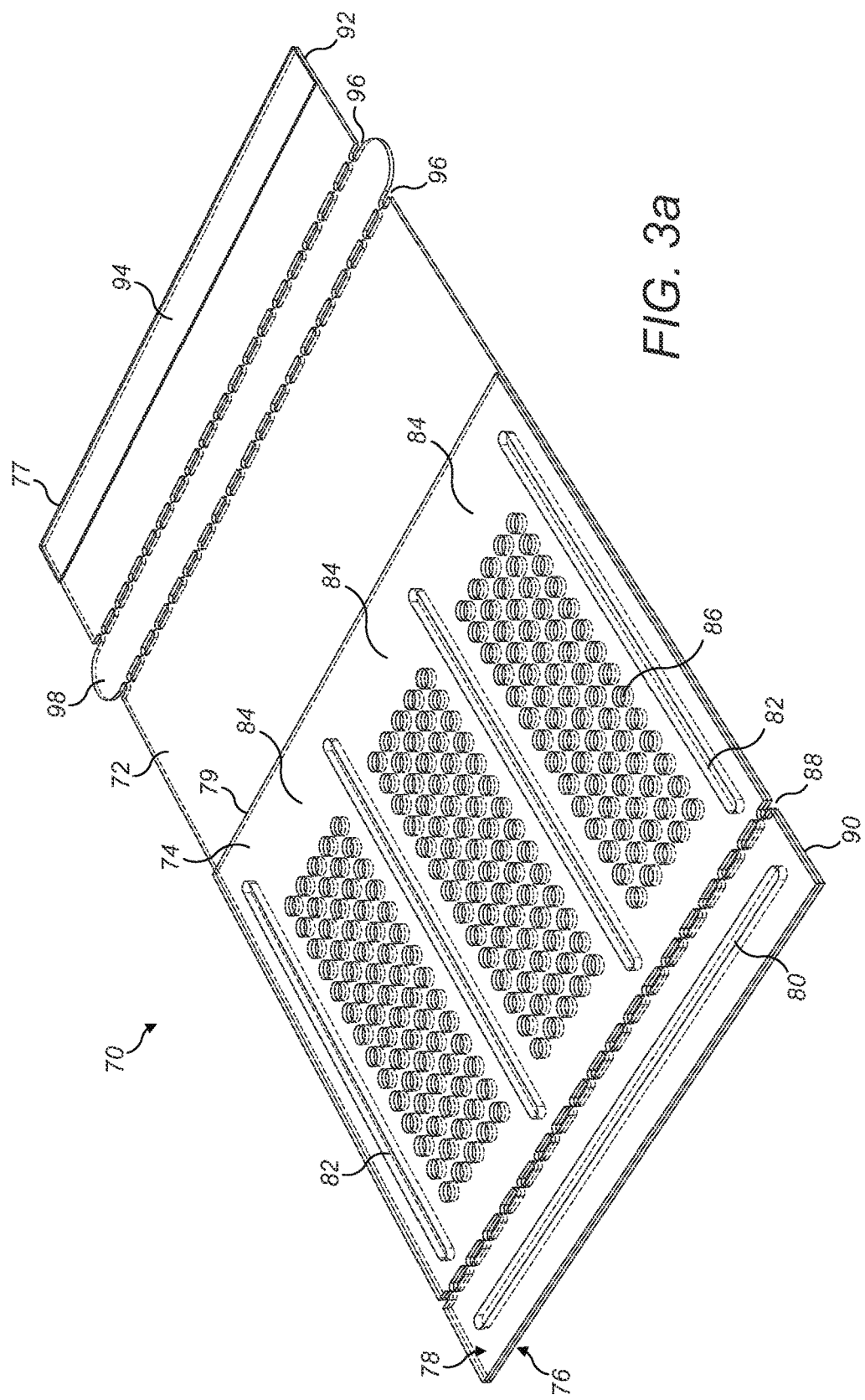

ENDOSCOPE VALVE CONTAINER

The present invention relates to a container for storing endoscope valves.

After an endoscope is used, it is necessary to clean and high level disinfect it before it can be re-used. During this cleaning and disinfection process, the endoscope is typically partially disassembled to ensure that some of the components inside the endoscope, such as the valves, are accessible during the reprocessing procedure.

When these valves are removed from the endoscope, they are typically kept together in a single chambered container during the cleaning/disinfection process, remaining with the endoscope for traceability purposes. Once the reprocessing is finished, the valves are then placed back into the endoscope and the container disposed of.

Whilst these containers serve their intended purpose of keeping the valves together, placing the valves together inside the container reduces the effectiveness of the cleaning process on the valves themselves.

Accordingly, the present invention provides a single-use container for holding a plurality of endoscope valves during a cleaning and disinfection procedure, the container defining a plurality of chambers which are isolated from each other and configured to receive a single valve such that a valve in one chamber cannot contact a valve in another chamber, a plurality of apertures in each chamber to allow fluid flow through the chamber, a closure device a single-use container for holding a plurality of endoscope valves during a cleaning and disinfection procedure, the container defining a plurality of chambers which are isolated from each other and configured to receive a single valve such that a valve in one chamber cannot contact a valve in another chamber, a plurality of apertures in each chamber to allow fluid flow through the chamber, a closure device operable to close each chamber, and an attachment device configured for attaching the container to an endoscope and preventing detachment without breaking of the attachment device.

By isolating the valves so that they cannot contact each other whilst in the container, the effectiveness of the cleaning process on each valve is improved. In addition, once the attachment device is in place the container cannot be detached from an endoscope without breaking the attachment device to ensure the entire container can only be used once, and to ensure the attachment is secure and the container cannot be detached and accidentally reattached to a different instrument.

The container may comprise first and second sheets of flexible material which are joined together in certain areas in order to define a plurality of chambers between the sheets. The use of first and second sheets of flexible material allow the container to be provided in a flat packed state prior to use, allowing the container to be stored in a smaller space prior to use.

In this embodiment, the closure device may also act as the attachment device, in which case the container further comprises a separate breakable opening device to allow opening of the chambers independent of the closure device.

In particular, the container may further comprise a perforated strip which defines a detachable portion of the container, wherein removal of the detachable portion allows access to the chambers. The perforated strip thus allows a single-use entry means into the chambers of the container.

In this embodiment, the closure means may comprise a flap formed by part of at least one of the sheets and configured to be folded over and secured to one of the sheets by adhesive.

The flap may be sufficiently long that it can be looped around part of an endoscope in order to form the attachment means connecting the container to the endoscope. By providing a suitable mechanism for attaching the container to the endoscope, this ensures that the valves cannot become separated from the endoscope from where they originated.

In an alternative embodiment, the container may comprise a base portion and the closure means may comprise a lid portion, each defining a volume and having au least one dividing wall, wherein the dividing walls of the base portion and lid portion cooperate in the closed condition to divide the volume into the separate chambers.

In yet another embodiment, the container may comprise a base portion and the closure means may comprise a lid portion, wherein the base portion is configured as a plurality of cups each defining a chamber, each cup having a rim and each rim being joined to the rim of an adjacent cup, and the lid portion is operable to close all the cups.

Each chamber of the container may comprise at least one support structures operable to engage a valve inserted into the chamber and to hold the valve in a fixed position. With the support structure, the held valves cannot rattle around inside their respective chambers. Thus the support structures further improve the effectiveness of the cleaning process.

The container may further comprise locking means to prevent opening of the closure means without breaking of the locking means. By including a locking means, the container is better protected from tampering and also premature opening during the cleaning process. The locking means also prevents the container from subsequently being reused.

Where a locking means is included, this may comprise a ratchet mechanism. This is a convenient way to provide a single use locking means.

The ratchet mechanism may comprise a flexible, elongate, toothed strip and a cooperating pawl, wherein the strip is sufficiently long and flexible that it can be looped around part of an endoscope in order to form the attachment means for connecting the container to an endoscope. Together, the strip and the pawl provide an intuitive and easy to use locking means.

Figure 1C:
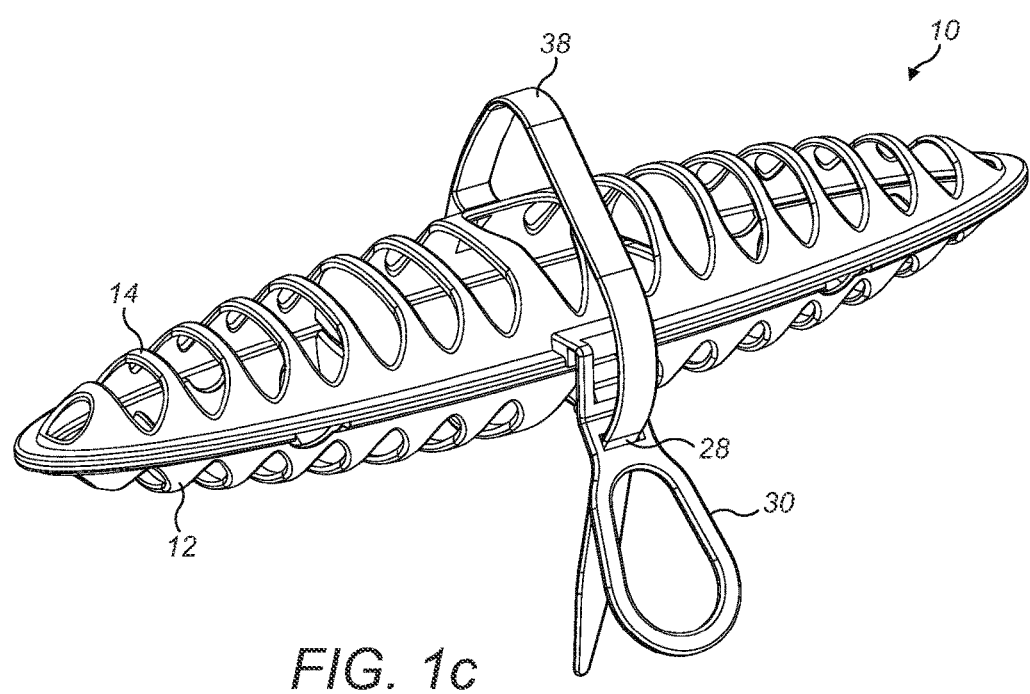

The invention will now be described, by example only, with reference to the accompanying drawings in which:

FIGS. 1a-c show perspective views of a first embodiment of a container according to the invention.

Figure 2A:
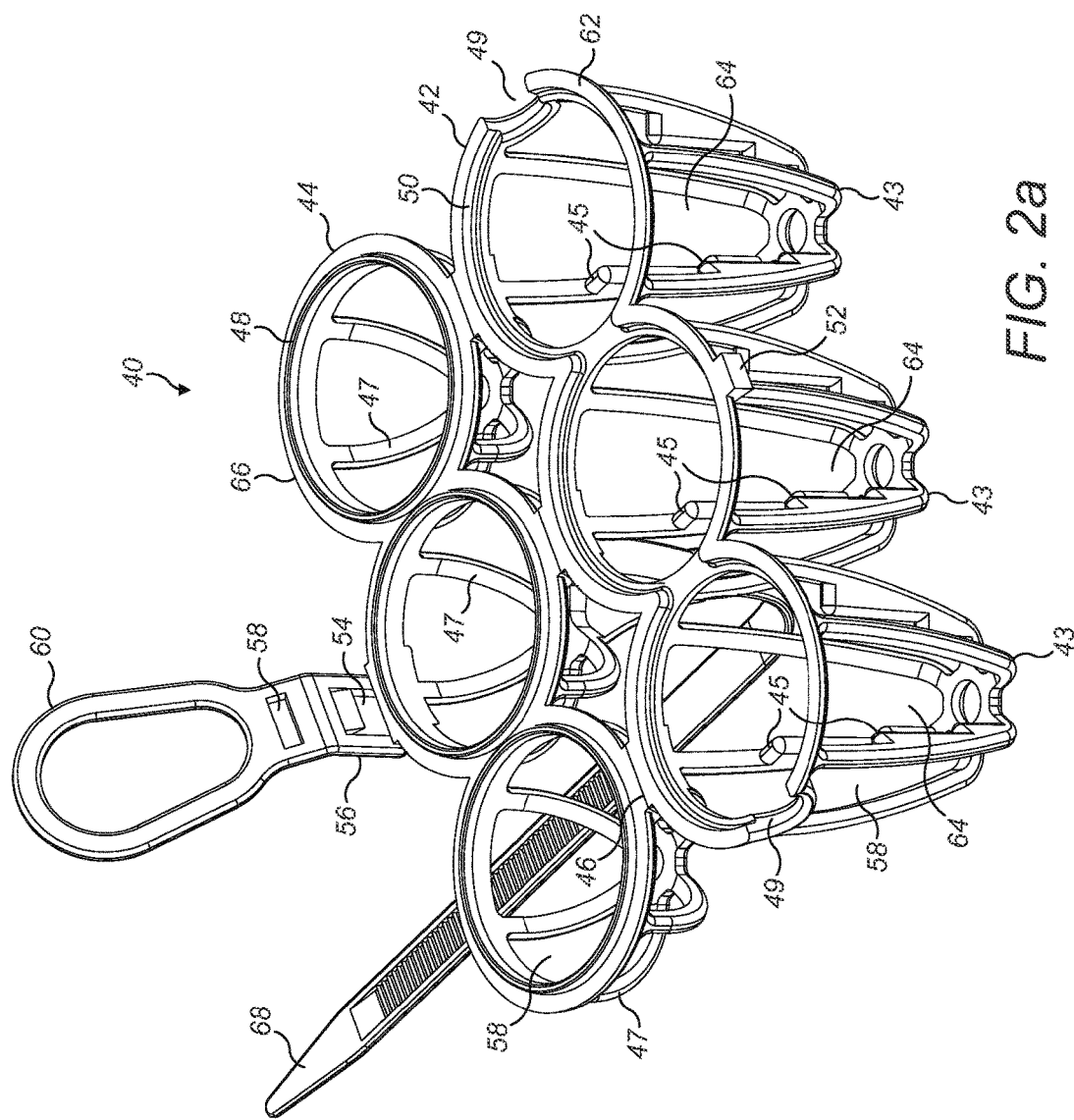
Figure 2B:
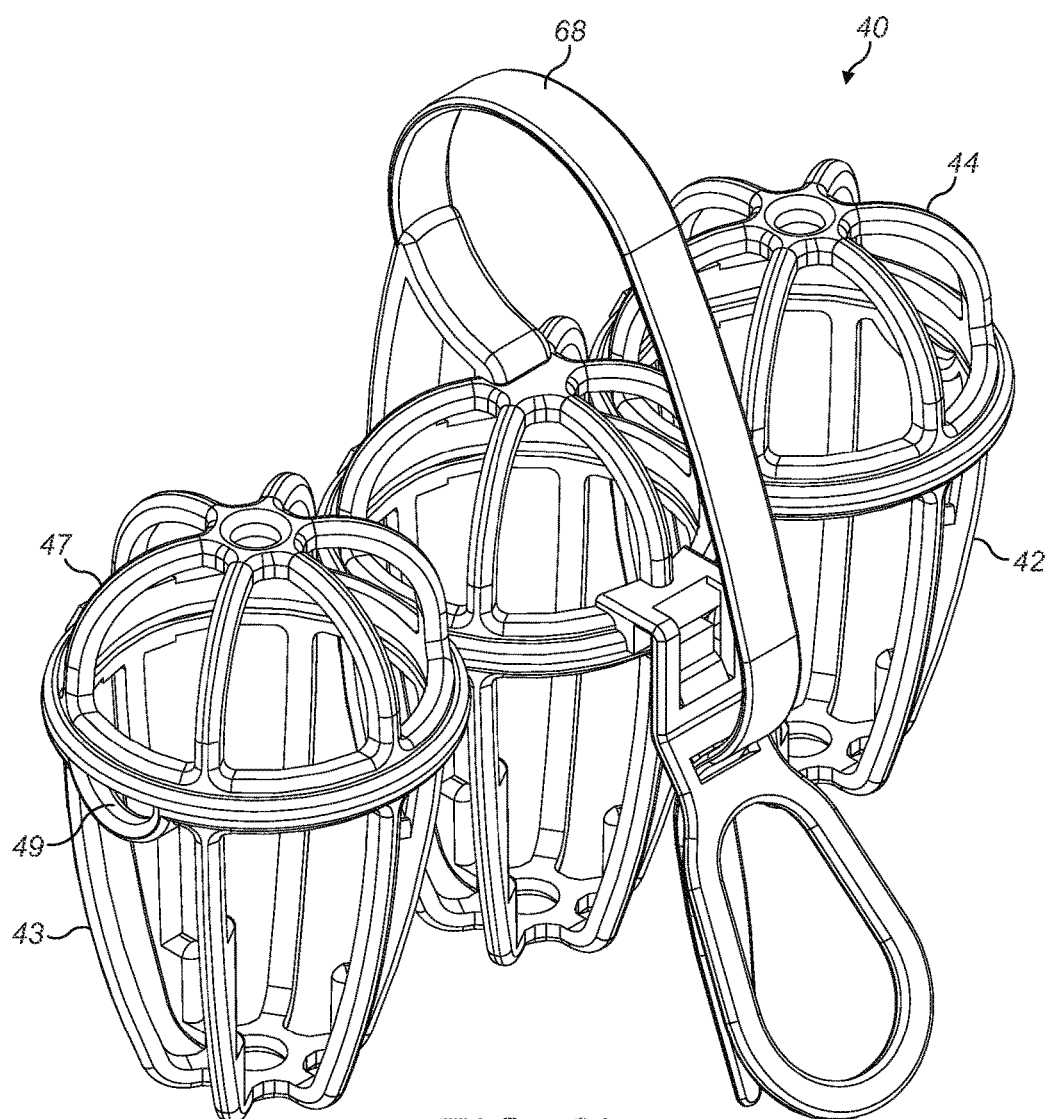

FIGS. 2a-b show perspective views of a second embodiment of a container according to the invention.

Figure 3B:
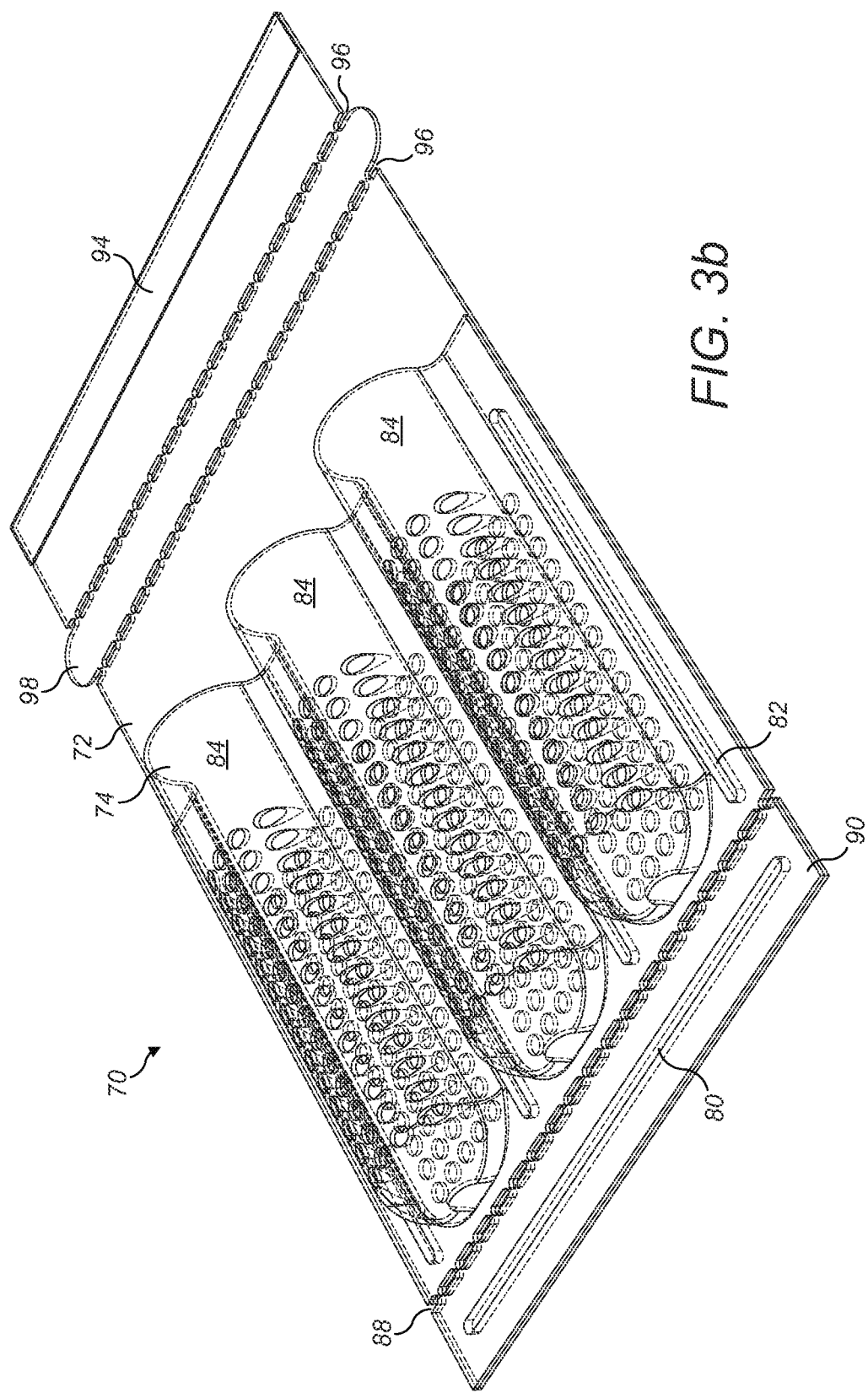
Figure 3C:
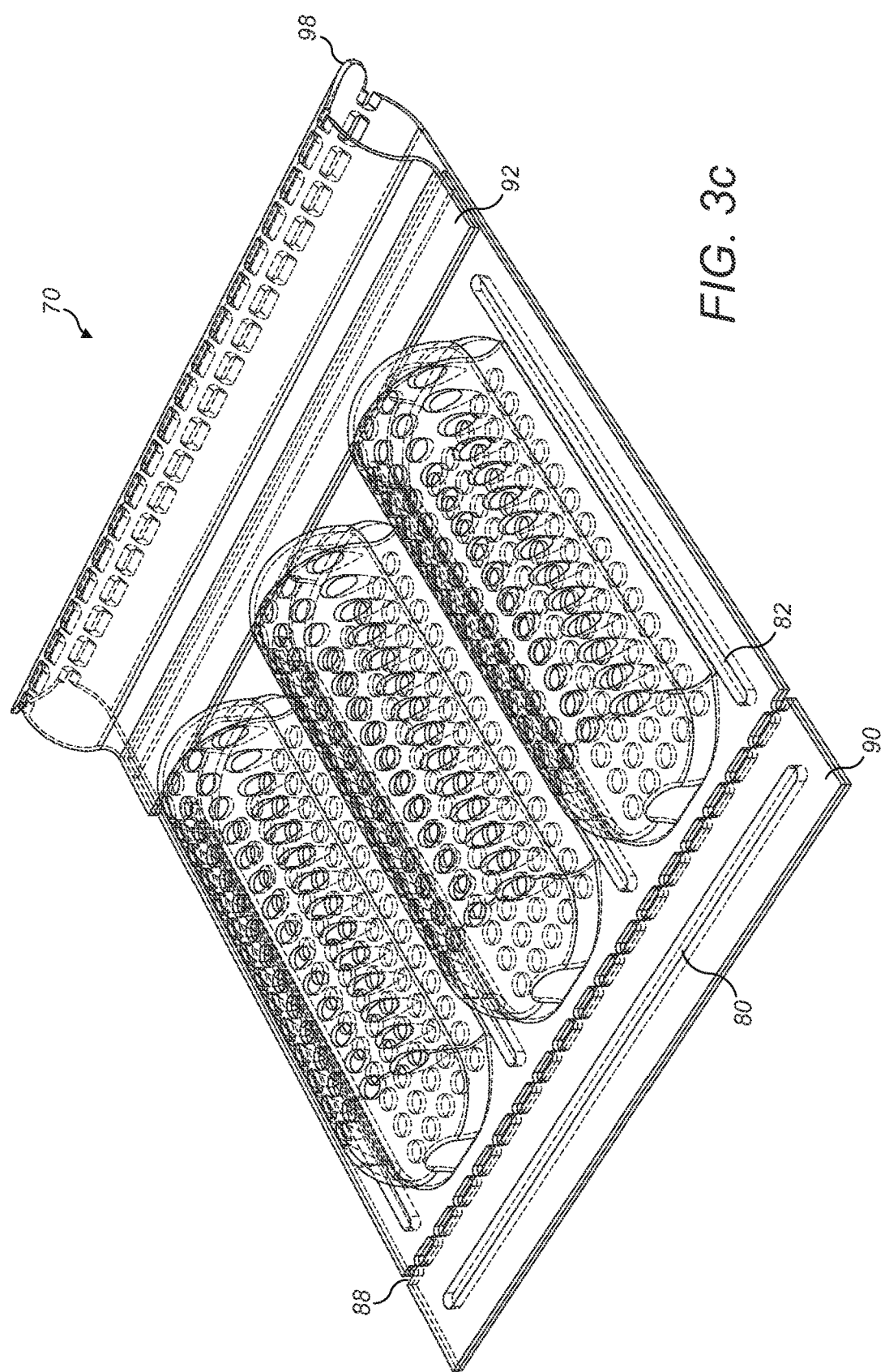

FIGS. 3a-c show perspective views of a third embodiment of a container according to the invention.

FIGS. 1a-c show a first embodiment of a container 10 for holding a plurality of endoscope valves. The container 10 is formed of two main parts: a base 12 and a lid 14. As shown in FIG. 1A, each of the base 12 and the lid 14 form half of a hollow ovoid which are connected together along one side by a hinge mechanism 16. When the lid 14 and base 12 are closed together, a ridge 18 extending around the circumference of the lid 14 engages with a corresponding groove 20 on the circumference of the base 12.

The base 12 and the lid 14 are secured together by a protrusion 22 on the base 12 which engages with a corresponding recess 24 in a tab 26 which extends from the lid 14. The protrusion 22 and recess 24 may have cooperating shapes such that once engaged they cannot be disengaged without breaking. This ensures the container 10 can only be used once. The tab 26 also includes an aperture 28 (described below) and an enlarged end 30 which simply makes it easy to grasp in use.

Inside each of the base 12 and the lid 14 are a series of partition walls 32. When the container 10 is in the closed position, the partition walls 32 from each of the base 12 and the lid 14 align so as to divide the interior of the container 10 into a series of chambers 34 (three chambers as shown in FIG. 1a). Each chamber 34 is dimensioned to receive one endoscope valve.

To allow fluid to pass into the container 10 when the base 12 and lid 14 are secured together, each of the base 12 and the lid 14 comprise a plurality of apertures 36 which are appropriately sized to allow fluid flow therethrough but small enough to not allow the valves to fall out from the container.

One or more generally semi-circular cut-outs 19 are preferably provided in the rim of the base 12. In this example, our cut-outs 19 are provided, two in the left-hand compartment and two in the right-hand compartment, with none in the central compartment. However, the shape, number and location of these cut-outs 19 can be varied as desired. During cleaning of an endoscope, when the normal valves have been removed, a cleaning adaptor valve is fitted to the endoscope to hold open the various channels in the endoscope to ensure effective cleaning. From time to time, this cleaning adaptor valve must itself be cleaned and on those occasions it is placed in the container 10. However, the cleaning adaptor valve must never be fitted to the endoscope when it is to be used. Therefore, such cleaning adaptor valves are fitted with a warning label, usually attached by a chain, to clearly identify it and differentiate it from the other valves. The cut-outs 19 are used when such a cleaning adaptor valve is placed into the container 10 for cleaning. The cut-outs 19 allow the chain to pass to the outside of the container so that the label is held outside, well clear of the cleaning adaptor valve, and does not get in the way of the cleaning process.

Extending from the base 12 is a flexible elongate strip 38 with a toothed portion 39. The flexible strip 38 can be passed through the aperture 28 in the tab 26. The teeth of the toothed portion 39 are shaped to engage with the edges of the aperture 28 such that once through the aperture 28, the flexible strip 38 can only be advanced further through it and cannot be withdrawn. Thus the toothed portion 39 and edges of aperture 28 act as a ratchet and pawl mechanism, in the manner of a conventional plastic cable tie.

In use the container 10 is first opened into the position shown in FIG. 1a. A used valve is placed lying down into each of the partitioned chambers 34 inside the base 12. The lid 14 is then closed over the base 12 such that the ridge 18 on the lid 14 engages with the groove 20 on the base 12. When the lid 14 is fully closed, the recess 24 is secured over the protrusion 22 on the base 12 to keep the container 10 closed.

To further lock the container 10 in this closed position, the flexible strip 38 extending from the base 12 is looped around as shown in FIG. 1b and passed through the aperture 28 as shown in FIG. 1c. The toothed portion 39 is then tightened against the edges of aperture 28 to lock the base 12 and the lid 14 together.

To ensure that the valves do not become separated from the endoscope from which they originated, during the looping of the flexible strip 38 around the base 12 and the lid 14, the flexible strip 38 may be further looped around a portion of the endoscope itself. This way, when the flexible strip 38 is tightened against the edges of the aperture 28, the container 10 is secured to the endoscope.

Once the container 10 is locked, it can placed through any suitable fluid disinfection process. Where such disinfection process involves using liquid or gaseous chemicals, the apertures 28 allows these chemicals to circulate freely through the container 10 and make contact with the valves located inside. Because the valves cannot touch each other during the disinfection process, there is a reduced risk of cross contamination between each of the valves during the disinfection process. Thus the effectiveness of the process on each valve is improved.

After the disinfection process is complete and the valves inside the container 10 are disinfected, the flexible strip 38 must be severed to allow the container 10 to be opened and the valves to be removed. This serves several purposes. First, an unsevered flexible strip provides evidence that the valves have not been tampered with whilst located inside the container 10. Second, it prevents the container 10 from being reused since the flexible strip 38 is not replaceable, because it is integral with the container 10. Third, it ensures that the endoscope is kept together with its dedicated valves, since the container cannot be detached from an endoscope and accidentally reattached to a different one.

Once the flexible strip 38 has been severed, the protrusion 22 is disengaged from the recess 24 to allow the base 12 and the lid 14 to be opened, and the valves removed from the container 10. The container 10, which now has a broken flexible strip 38, is then disposed of.

Turning to FIGS. 2a-c, there is shown a second embodiment container 40 for holding a plurality of endoscope valves.

As with the first container 10, the second container 40 comprises a base 42 and a lid 44 which are connected together along one side via a hinge mechanism 46. The base 42 and the lid 44 are secured together by a protrusion 52 on the base 42 which engages with a corresponding recess 54 on a tab 56 which protrudes from the lid 44. The tab 56 of this container 40 also comprises an aperture 58 and an enlarged end 60.

The second container 40 also comprises a flexible elongate toothed strip 68 which is operable to engage with the aperture 58 in the tab 56. In this example, the flexible strip 68 is connected to both the base 42 and the lid 44 portions of the container 40.

In the second container 40 however, the base 42 is formed as a series of individual cups 43, arranged side by side, which each provide a chamber 64 for storing a valve in an upright position. Inside each of the cups 43 is a series of stepped shoulders 45. These are arranged and dimensioned to engage against a valve inserted into the cup 43 to hold it in a substantially upright position, while keeping the contact area of each shoulder 45 against the valve as small as possible so that the vast majority of the valve surfaces can still be contacted by the cleaning and sterilising fluid.

The lid 44 also consists of a series of adjacent cups 47, typically more shallow that the cups 43 forming the base 42. The lid cups 47 may also include shoulders for engaging against a valve, although they are not shown in this example. The rim 62 of each base cup 43 includes a groove 50 for engaging with a corresponding ridge 48 extending around the rim 66 of each lid cup 47.

As with the first embodiment, the base 42 and the lid 44 each contain apertures 58 which are appropriately sized to allow fluid flow to freely circulate therethrough, but small enough to not allow the valves to fall out from the container 40. In the second embodiment however, because movement of each of the valves is restricted inside the cups 43 by the shoulders 45, the apertures 58 can be much larger than the apertures 28 from the first embodiment without an increased risk of the valves falling out of the cups 43 through one of these apertures 58.

In this embodiment, as with the first embodiment, one or more cut-outs 49 may be provided in the rim of the base 42, in order to accommodate a chain attaching a label to a cleaning adaptor valve placed into the container 40. In this example, the left-hand and right-hand cups 43 each have one cut-out 49, although the number and location of the cut-outs 49 can be varied as desired.

Operation of the second container 40 is identical to that of the first container 10, except for the fact that the valves are held in individual cups 43 and in an upright position, rather than lying down in each of the chambers 34 as in the first container 10. Once the second container 40 has been used and the flexible strip severed, the container 40 is then disposed of.

In relation to FIGS. 3a-c, there is provided a third embodiment of a container 70 for holding endoscope valves.

The third embodiment of container 70 is formed of first and second sheets of thin, flexible material 72, 74, such as plastic film, which are partially joined together to form an array of pockets 84 which each are sized to receive an endoscope valve.

The first and second sheets 72, 74 are adhered together in various regions in order to create separate pockets 84. In this example, the first and second sheets 72, 74 are substantially rectangular with first ends 76, 78 and second ends 77, 79. The second sheet 74 overlies the first sheet 72 with their first ends 76, 78 aligned. However, the second sheet is shorter and so the second end 77 of the first sheet 72 extends beyond the second end 79 of the second sheet 74.

The two sheets 72, 74 are secured together adjacent to their first ends 76, 78, for example by adhesive or heat bonding, along a line 80. Further bonding lines 82, which are generally perpendicular to the end bonding line 80, join the two sheets 72, 74 and create a series of pockets 84 between them. In this example, four bonding lines 82 create three pockets 84. In the region of each pocket 84, the sheets 72, 74 are provided with an array of apertures 86.

Between the end bonding line 80 and the perpendicular bonding lines 82, a line of perforations 88 extends across both sheets 72, 74 to create a first tear off strip 90.

At the second end 77 of the first sheet 72 is an adhesive strip 92 protected by a releasable peel-off cover paper 94. A pair of perforated lines 96 extend across the first sheet 72, between the adhesive strip 92 and the second end 79 of the second sheet 74. The pair of perforated lines 96 define between them a tearaway tab 98.

In use, the two sheets 72, 74 can be partially separated to open out the pockets 84 as shown in FIG. 3b. An endoscope valve can then be inserted between the sheets 72, 74 into each pocket 84. The second end 77 of the first sheet 72 can then be folded over, the cover paper 94 peeled off and the adhesive strip 92 secured to the second end 79 of the second sheet 74, thus closing the pockets 84 to retain a valve in each pocket 84 as shown in FIG. 3c. As the second end 77 of the first sheet 72 is folded over, it can also be looped around part of an endoscope in order to secure the container 70 to the endoscope. The endoscope and container 70 can then be passed through a conventional cleaning and disinfection process, with the apertures 86 in the sheets 72, 74 allowing fluid to circulate around the valves in the pockets 84.

Once the disinfection process is complete, the tab 98 can be torn away along perforation lines 96 in order to release the container 70 from the endoscope. The strip 90 can also be torn away along perforation line 88 to allow access to the pockets 84 for removal of the valves. The container 70 can then be disposed of.

This third embodiment of container 70 has particular advantages in that it is easy and cost effective to manufacture and a large number of containers can be stored flat for maximum space efficiency.

Although the above can be used as an illustrative guide to the present invention, it will be appreciated by those skilled in the art that variations and modifications can be made without departing from the scope of the invention as set out in the claims. For instance, each of the containers need not necessarily be limited to use solely with endoscope valves. Similarly, it will be appreciated that each of the containers could have any number of chambers, and that each of the chambers need not necessarily be the same size. The containers may be made from any suitable material which can withstand the cleaning and disinfection process, for example the first and second embodiments may be injection moulded plastic and the third embodiment produced from plastic film.

The invention claimed is:

1. A single-use container attachable to an endoscope for holding a plurality of endoscope valves during a cleaning and disinfection procedure, the container comprising first and second sheets of flexible material which are joined together in certain areas in order to define a plurality of chambers between the sheets which are isolated from each other and configured to receive a single valve such that a valve in one chamber cannot contact a valve in another chamber, and a closure device operable to close each chamber to secure the valves in the chambers during the cleaning and disinfecting procedure; characterized by a plurality of apertures in each chamber which are appropriately sized to allow liquid to flow freely through the chamber during the cleaning and disinfecting procedure, and an attachment device configured for attaching the container to an endoscope and preventing detachment of the container from the endoscope during the cleaning and disinfecting procedure without breaking of the attachment device.

2. A container as claimed in claim 1, wherein the closure device also acts as the attachment device and the container further comprises a separate breakable opening device to allow opening of the chambers independently of the closure device.

3. A container as claimed in claim 2, wherein the breakable opening device comprises a perforated strip which defines a detachable portion of the container, wherein removal of the detachable portion allows access to the chambers.

4. A container as claimed in any of claim 1, wherein the closure device comprises a flap formed by part of at least one of the sheets and configured to be folded over and secured to one of the sheets by adhesive.

5. A container as claimed in claim 4, wherein the flap is sufficiently long that it can be looped around part of an endoscope in order to form the attachment device for attaching the container to an endoscope.

6. A container as claimed in claim 1, further comprising locking means to prevent opening of the closure device without breaking of the locking means during the cleaning and disinfecting procedure.

* * * * *